(12) United States Patent
Xue et al.

(10) Patent No.: US 7,966,058 B2
(45) Date of Patent: Jun. 21, 2011

(54) SYSTEM AND METHOD FOR REGISTERING AN IMAGE WITH A REPRESENTATION OF A PROBE

(75) Inventors: Joel Q. Xue, Germantown, WI (US); Wenguang Li, Sugarland, TX (US)

(73) Assignee: General Electric Company, Schenectady, NY (US)

( * ) Notice: Subject to any disclaimer, the term of this patent is extended or adjusted under 35 U.S.C. 154(b) by 2276 days.

(21) Appl. No.: 10/749,540

(22) Filed: Dec. 31, 2003

(65) Prior Publication Data
US 2005/0154281 A1    Jul. 14, 2005

(51) Int. Cl.
*A61B 5/055* (2006.01)
*A61B 8/00* (2006.01)
*G06K 9/32* (2006.01)

(52) U.S. Cl. ........ 600/427; 600/407; 600/425; 600/443; 382/294

(58) Field of Classification Search ........... 600/407, 600/410, 411, 427, 437, 443, 374, 587, 425; 606/32; 607/122; 382/128, 276, 294, 298
See application file for complete search history.

(56) References Cited

U.S. PATENT DOCUMENTS

| | | | |
|---|---|---|---|
| 4,849,692 A | 7/1989 | Blood | |
| 4,945,305 A | 7/1990 | Blood | |
| 5,297,549 A | 3/1994 | Beatty et al. | |
| 5,311,866 A | 5/1994 | Kagan et al. | |
| 5,391,199 A | 2/1995 | Ben-Haim | |
| 5,443,066 A | 8/1995 | Dumoulin et al. | |
| 5,443,489 A | 8/1995 | Ben-Haim | |
| 5,445,150 A | 8/1995 | Dumoulin et al. | |
| 5,480,422 A | 1/1996 | Ben-Haim | |
| 5,487,391 A * | 1/1996 | Panescu | 600/512 |
| 5,515,853 A | 5/1996 | Smith et al. | |
| 5,546,951 A | 8/1996 | Ben-Haim | |
| 5,553,611 A | 9/1996 | Budd et al. | |
| 5,558,091 A | 9/1996 | Acker et al. | |
| 5,568,809 A | 10/1996 | Ben-Haim | |
| 5,600,330 A | 2/1997 | Blood | |
| 5,602,891 A * | 2/1997 | Pearlman | 378/62 |
| 5,662,108 A * | 9/1997 | Budd et al. | 600/374 |
| 5,676,673 A | 10/1997 | Ferre et al. | |
| 5,694,945 A | 12/1997 | Ben-Haim | |
| 5,697,377 A | 12/1997 | Wittkampf | |
| 5,713,946 A | 2/1998 | Ben-Haim | |
| 5,718,241 A | 2/1998 | Ben-Haim et al. | |
| 5,722,402 A | 3/1998 | Swanson et al. | |
| 5,729,129 A | 3/1998 | Acker | |
| 5,738,096 A | 4/1998 | Ben-Haim | |
| 5,744,953 A | 4/1998 | Hansen | |

(Continued)

OTHER PUBLICATIONS

*Cardiac catheterization system*, Cardiac Cath Lab Systems, RMC-3100, RMC-3200, printed from website www.nihonkohden,com on Dec. 18, 2003, (2 pgs.).

(Continued)

*Primary Examiner* — Long V Le
*Assistant Examiner* — Katherine L Fernandez
(74) *Attorney, Agent, or Firm* — William Kryger

(57) ABSTRACT

A system and method is provided for registering a representation of a probe with an image. One embodiment of a method comprises acquiring an image of or pertaining to a heart and registering a representation of a probe which is in or adjacent to the heart with the image using a heart vector of the heart.

13 Claims, 5 Drawing Sheets

U.S. PATENT DOCUMENTS

| | | | |
|---|---|---|---|
| 5,752,513 A | 5/1998 | Acker et al. | |
| 5,779,638 A | 7/1998 | Vesely et al. | |
| 5,795,298 A | 8/1998 | Vesely et al. | |
| 5,797,849 A | 8/1998 | Vesely et al. | |
| 5,800,352 A | 9/1998 | Ferre et al. | |
| 5,803,089 A | 9/1998 | Ferre et al. | |
| 5,813,991 A | 9/1998 | Willis et al. | |
| 5,817,022 A | 10/1998 | Vesely | |
| 5,820,568 A | 10/1998 | Willis | |
| 5,829,444 A | 11/1998 | Ferre et al. | |
| 5,830,144 A | 11/1998 | Vesely | |
| 5,833,608 A | 11/1998 | Acker | |
| 5,840,025 A | 11/1998 | Ben-Haim | |
| 5,846,198 A * | 12/1998 | Killmann | 600/424 |
| 5,868,673 A | 2/1999 | Vesely | |
| 5,873,822 A | 2/1999 | Ferre et al. | |
| 5,916,163 A | 6/1999 | Panescu et al. | |
| 5,928,248 A | 7/1999 | Acker | |
| 5,953,683 A | 9/1999 | Hansen et al. | |
| 5,967,980 A | 10/1999 | Ferre et al. | |
| 5,983,126 A * | 11/1999 | Wittkampf | 600/509 |
| 5,997,883 A * | 12/1999 | Epstein et al. | 324/306 |
| 6,016,439 A | 1/2000 | Acker | |
| 6,019,725 A | 2/2000 | Vesely et al. | |
| 6,066,094 A | 5/2000 | Ben-Haim | |
| 6,147,480 A | 11/2000 | Osadchy et al. | |
| 6,161,032 A | 12/2000 | Acker | |
| 6,175,756 B1 | 1/2001 | Ferre et al. | |
| 6,183,088 B1 | 2/2001 | LoRe et al. | |
| 6,188,355 B1 | 2/2001 | Gilboa | |
| 6,188,924 B1 | 2/2001 | Swanson et al. | |
| 6,198,963 B1 | 3/2001 | Haim et al. | |
| 6,211,666 B1 | 4/2001 | Acker | |
| 6,216,027 B1 | 4/2001 | Willis et al. | |
| 6,223,066 B1 | 4/2001 | Govari | |
| 6,226,542 B1 | 5/2001 | Reisfeld | |
| 6,226,543 B1 | 5/2001 | Gilboa et al. | |
| 6,240,307 B1 | 5/2001 | Beatty et al. | |
| 6,246,231 B1 | 6/2001 | Ashe | |
| 6,246,898 B1 | 6/2001 | Vesely et al. | |
| 6,248,075 B1 | 6/2001 | McGee et al. | |
| 6,256,540 B1 | 7/2001 | Panescu et al. | |
| 6,266,551 B1 | 7/2001 | Osadchy et al. | |
| 6,285,898 B1 | 9/2001 | Ben-Haim | |
| 6,301,496 B1 * | 10/2001 | Reisfeld | 600/407 |
| 6,314,310 B1 | 11/2001 | Ben-Haim et al. | |
| 6,332,089 B1 | 12/2001 | Acker et al. | |
| 6,335,617 B1 | 1/2002 | Osadchy et al. | |
| 6,341,231 B1 | 1/2002 | Ferre et al. | |
| 6,366,799 B1 | 4/2002 | Acker | |
| 6,368,285 B1 | 4/2002 | Osadchy et al. | |
| 6,370,411 B1 | 4/2002 | Osadchy et al. | |
| 6,373,240 B1 | 4/2002 | Govari | |
| 6,379,302 B1 | 4/2002 | Kessman et al. | |
| 6,380,732 B1 | 4/2002 | Gilboa | |
| 6,385,476 B1 | 5/2002 | Osadchy et al. | |
| 6,400,981 B1 | 6/2002 | Govari | |
| 6,427,314 B1 | 8/2002 | Acker | |
| 6,445,943 B1 | 9/2002 | Ferre et al. | |
| 6,447,504 B1 | 9/2002 | Ben-Haim et al. | |
| 6,453,190 B1 | 9/2002 | Acker et al. | |
| 6,456,867 B2 | 9/2002 | Reisfeld | |
| 6,458,123 B1 | 10/2002 | Brucker et al. | |
| 6,484,049 B1 | 11/2002 | Seeley et al. | |
| 6,484,118 B1 | 11/2002 | Govari | |
| 6,487,441 B1 | 11/2002 | Swanson et al. | |
| 6,489,961 B1 | 12/2002 | Baxter, III et al. | |
| 6,490,468 B2 | 12/2002 | Panescu et al. | |
| 6,490,474 B1 * | 12/2002 | Willis et al. | 600/424 |
| 6,490,475 B1 | 12/2002 | Seeley et al. | |
| 6,496,712 B1 | 12/2002 | Dahl et al. | |
| 6,498,477 B1 | 12/2002 | Govari et al. | |
| 6,498,944 B1 | 12/2002 | Ben-Haim et al. | |
| 6,516,807 B1 | 2/2003 | Panescu et al. | |
| 6,522,913 B2 | 2/2003 | Swanson et al. | |
| 6,528,991 B2 | 3/2003 | Ashe | |
| 6,546,270 B1 | 4/2003 | Golden et al. | |
| 6,558,333 B2 | 5/2003 | Gilboa et al. | |
| 6,565,511 B2 | 5/2003 | Panescu et al. | |
| 6,569,160 B1 | 5/2003 | Goldin et al. | |
| 6,574,492 B1 * | 6/2003 | Ben-Haim et al. | 600/374 |
| 6,600,948 B2 * | 7/2003 | Ben-Haim et al. | 600/512 |
| 6,892,091 B1 * | 5/2005 | Ben-Haim et al. | 600/509 |
| 6,896,657 B2 * | 5/2005 | Willis | 600/437 |
| 6,970,733 B2 * | 11/2005 | Willis et al. | 600/424 |
| 7,189,208 B1 * | 3/2007 | Beatty et al. | 600/587 |
| 7,505,809 B2 * | 3/2009 | Strommer et al. | 600/424 |
| 2001/0044585 A1 * | 11/2001 | Dupree et al. | 600/509 |
| 2002/0072670 A1 * | 6/2002 | Chenal et al. | 600/449 |
| 2002/0120192 A1 * | 8/2002 | Nolte et al. | 600/424 |
| 2005/0154281 A1 * | 7/2005 | Xue et al. | 600/407 |

OTHER PUBLICATIONS

*DASH PRO, Variable-Acuity Monitoring*, GE Medical Systems Information Technologies, 02-7446A, Mar. 2002, (8 pgs.).

*GE Announces Alliance with Biosense Webster to Give Clinicians Access to Patients' Complete Heart Rhythm Data at a Single Workstation*, GE Medical Systems—Company News-News Releases, dated May 15, 2003, (2 pgs.).

*Invasive—CardioLink Networking—Boosts your productivity*, GE Medical Systems, Europe, Middle East & Africa, printed from website www.gemedicalsystemseurope.com/euen/cardiology/invasive/electro_la... on Jan. 27, 2004, (2 pgs.).

Navigation and Visualization, InstaTrak™—*Cranial Multi-application electromagnetic surgical navigation system for ENT, Cranial and Spine procedures*, GE Medical Systems, printed from website www.gemedicalsystemseurope.com/euen/rad/nav/instatrak_cranial_ho on Jan. 27, 2004, (2 pgs.).

Invasive, *Increase Efficiency in the Cardiac Cath Lab*, GE Medical Systems, printed from website www.gemedicalsystems.com/cardiology/invasive/cardiac_cath_lab/comb on Jan. 12, 2004, (1 pg.).

Invasive—CardioLab—5.1, *Bringing added functionality to the world class CardioLab EP System*, GE Medical Systems, printed from website www.gemedicalsystems.com/cardiology/invasive/electro_lab... on Jan. 12, 2004, (2 pgs.).

Computed Tomography, *Advanced Clinical Applications*, GE Medical Systems, printed from website www.gemedicalsystems.com/rad/ct/applications/msctappl.html on Jan. 28, 2004, (2 pgs.).

Computed Tomography, *Advanced CT Applications—Navigator*, GE Medical Systems, printed from website www.gemedicalsystems.com/rad/ct/applications/navigator.html on Jan. 28, 2004, (1 pg.).

Computed Tomography, *Advanced CT Applications—Direct3D*, GE Medical Systems, printed from website www.gemedicalsystems.com/rad/ct/applications/direct3d.html on Jan. 28, 2004, (1 pg.).

Computed Tomography, *Advanced CT Applications—Volume Rendering*, GE Medical Systems, printed from website www.gemedicalsystems.com/rad/ct/applications/vr.html on Jan. 28, 2004, (2 pgs.).

Computed Tomography, *Advanced CT Applications—Advantage Sim*, GE Medical Systems, printed from website www.gemedicalsystems.com/rad/ct/applications/sim_benefits.html on Jan. 28, 2004, (1 pg.).

Computed Tomography, *Advanced CT Applications—Advantage Sim (Simulation Tools)*, GE Medical Systems, printed from website www.gemedicalsystems.com/rad/ct/applications/sim_sim.html on Jan. 28, 2004, (1 pg.).

Computed Tomography, *Advanced CT Applications—Advantage Sim (Advanced CT Simulation)*, GE Medical Systems, printed from website www.gemedicalsystems.com/rad/ct/applications/sim.html on Jan. 28, 2004, (2 pgs.).

Computed Tomography, *GE Medical Systems is proud to offer Mindways QCT PRO 3D Volumetric Spine & Hip BMD—B7501MW—Accurate & Reproducible*, GE Medical Systems, printed from website www.gemedicalsystems.com/rad/ct/applications/bmd/index.html on Jan. 28, 2004, (1 pg.).

Computed Tomography, *Snapshot cardiac imaging provides the most flexible and widest range of clinical acquisition and reconstruction options available today. Snapshot enables cardiac imaging over a wide range of patients (from 40 to 110 bpm)*, GE Medical Systems, printed from website www.gemedicalsystems.com/rad/ct/applications/snapshot/index.html on Jan. 28, 2004, (1 pg.).

Computed Tomography, *SmartScore—Coronary Artery Calcification Scoring*, GE Medical Systems, printed from website www.gemedicalsystems.com/rad/ct/applications/smart_score/index.html on Jan. 28, 2004, (2 pgs.).
SmartScore, *Coronary Artery Calcification Scoring*, GE Medical Systems, copyright date: 2000, (6 pgs.).
Computed Tomography, *CardIQ Function—Cardiac Functional Analysis*, GE Medical Systems, printed from website www.gemedicalsystems.com/rad/ct/applications/cardiq_func/index.html on Jan. 28, 2004, (2 pgs.).
Computed Tomography, *CardIQ Analysis—CV Image Post-Processing & Analysis*, GE Medical Systems, printed from website www.gemedicalsystems.com/rad/ct/applications/cardiq/index.html on Jan. 28, 2004, (2 pgs.).
Computed Tomography, *Advanced Vessel Analysis*, GE Medical Systems, printed from website www.gemedicalsystems.com/rad/ct/applications/ava/ct_ava_home.html on Jan. 28, 2004, (2 pgs.).
Advanced Vessel Analysis—*Image Analysis Software*, GE Medical Systems, copyright date: 2000, (4 pgs.).
*B77OOSS Advanced Vessel Analysis*,—GE Medical Systems, date undetermined, (2 pgs.).
Advanced Vessel Analysis, Clinical Case Study, *Application in Pre-stent Graft Evaluation and Post-stent Graft Imaging*, GE Medical Systems, copyright date: 2000, (8 pgs.).
Advantage Workstation—*Multi-Modality Software Applications:*, GE Medical Systems, printed from website www.gemedicalsystems.com/rad/aw/aw_multisoft.html on Jan. 28, 2004, (3 pgs.).
Advantage Workstation—*CT Software Applications:*, GE Medical Systems, printed from website www.gemedicalsystems.com/rad/aw/aw_ctsoft.html on Jan. 28, 2004, (4 pgs.).
Advantage Workstation—*MR Software Applications:*, GE Medical Systems, printed from website www.gemedicalsystems.com/rad/aw/aw_mrsoft.html on Jan. 28, 2004, (2 pgs.).
Advantage Workstation—*Vascular Software Applications:*, GE Medical Systems, printed from website www.gemedicalsystems.com/rad/aw/aw_vascsoft.html on Jan. 28, 2004, (2 pgs.).
Functional Imaging—*POWERstation™ General Software*, GE Medical Systems, printed from website www.gemedicalsystems.com/rad/nm_pet/clinical_img/general.html on Jan. 28, 2004, (1 pg.).
Functional Imaging—*QuickSPECT™ Reconstruction*, GE Medical Systems, printed from website www.gemedicalsystems.com/rad/nm_pet/products/vision/qspectrecon.h... on Jan. 28, 2004, (2 pgs.).
Functional Imaging—*QuickSPECT™—ReadMaster Display*, GE Medical Systems, printed from website www.gemedicalsystems.com/rad/nm_pet/products/vision/qspectdisplay... on Jan. 28, 2004, (2 pgs.).
Functional Imaging—*VCR™*, GE Medical Systems, printed from website www.gemedicalsystems.com/rad/nm_pet/products/vision/vcrrecon.html on Jan. 28, 2004, (2 pgs.).
Functional Imaging—*3D Rendering*, GE Medical Systems, printed from website www.gemedicalsystems.com/rad/nm_pet/products/vision/3d.html on Jan. 28, 2004, (2 pgs.).
Functional imaging—*General Display*, GE Medical Systems, printed from website www.gemedicalsystems.com/rad/nm_pet/products/vision/qeneral_ displa... on Jan. 28, 2004, (2 pgs.).
Functional Imaging—*PC Graphics*, GE Medical Systems, printed from website www.gemedicalsystems.com/rad/nm_pet/products/vision/pc.html on Jan. 28, 2004, (2 pgs.).
Functional Imaging—*SPECT Triangulating Display*, GE Medical Systems, printed from website www.gemedicalsystems.com/rad/nm_pet/products/vision/spectl.html on Jan. 28, 2004, (2 pgs.).
Functional Imaging—*Color Scales*, GE Medical Systems, printed from website www.gemedicalsystems.com/rad/nm_pet/products/vision/color.html on Jan. 28, 2004, (2 pgs.).
Functional Imaging—*Image Processing*, GE Medical Systems, printed from website www.gemedicalsystems.com/rad/nm_pet/clinical_ img/imaqe_ processing. on Jan. 28, 2004, (2 pgs.).
*Prucka CardioLab/Mac-Lab 7000 CardioLink Operator's Manual*, GE Medical Systems, Revision C, marked as Jul. 2, 2001, (24 pgs.).
Realtime Position Management™, *Integrating Advanced Mapping, Navigation and EP Recording*, Boston Scientific, copyright date: 2003, Boston Scientific Corporation, (3 pgs.).
*Advanced Mapping*, Boston Scientific, printed from website www.bostonscientific.com/common_templates/procedureOverview.jhtml on Jan. 9, 2004, (2 pgs.).
*Diagnostic EP Study*, Boston Scientific, printed from website www.bostonscientific.com/common_ templates/procedureOverview.jhtml on Jan. 9, 2004, (2 pgs.).
*Pericardiocentesis*, Boston Scientific, printed from website www.bostonscientific.com/common_ templates/procedureOverview.jhtml on Jan. 9, 2004, (1 pg.).
*RF Ablation*, Boston Scientific, printed from website www.bostonscientific.com/common_ templates/procedureOverview.jhtml on Jan. 9, 2004, (2 pgs.).
*RPM Realtime Position Management™ System*, Boston Scientific, printed from website www.bostonscientific.com/med_specialty/deviceDetail.jhtml?task=tskBa ... on Jan. 12, 2004, (2 pgs.).
*RPM Realtime Position Management™ System*, (*Instructions for use*) Electrophysiology, Boston Scientific, printed from website www.bostonscientific.com/common_templates/singleDetailList.jhtml?tas on Jan. 12, 2004, (2 pgs.).
*How to Get There From Here*, Pruka Cardiolab 7000, Advanced Electrophysiology Diagnostic System, GE Medical Systems, copyright date: 2000, (2 pgs.).
Jasbir Sra, Joy Thomas, *New Techniques for Mapping Cardiac Arrhythmias*, Indian Heart Journal, Jul.-Aug. 2001, printed from website www.indianheartjournal.org/JulyAuqust2001/New_ Techniquesfor Mapping/... on Jan. 19, 2004, (30 pgs.).
*EP MedSystems Submits 510-K- Filing for Integration of Catheter Navigation Technology into EP-Workmate Platform*, West Berlin, N.J.—(Business Wire), Jul. 24, 2003, printed from website www.businesswire.com/webbox/bw.072403/232055085.htm on Jan. 19, 2004, (1 pg.).
Anoop K. Gupta, Alok Maheshwari, Ranjan K. Thakur, Yash Y. Lokhandwala, *Catheter Ablation of Atrial Tachycardia Using a Real-Time Position Management Mapping System*, Indian Heart Journal, Jan.-Feb. 2003, printed from website www.indianheartjournal.org/Jan-Feb2003/Catheter%20Ablation%20of%... on Jan. 19, 2004, (4 pgs.).
Products / EPWorkMate®—*The Completely Integrated EP WorkStation*, EPMedSystems, copyright date: 2001, printed from website www.epmedsystems.com/products/epwm/index.htm on Jan. 19, 2004, (4 pgs.).
*INVASIVE—CardioImage Fluoroscopy Image Management System*, GE Medical Systems, printed from website www.gemedicalsystem.com/cardiology/invasive/electro_lab/cardioimag... on Jan. 26, 2004, (1 pg.).
*Maximum Access to Patient Data*, Heartlab, printed from website www.heartlab.com/benefits_access.htm on Jan. 27, 2004, (1 pg.).
*Superior Performance, System Stability And On-Going Maintainability*, Heartlab, printed from website www.heartlab.com/benefits_performance.htm on Jan. 27, 2004, (1 pg.).
*Unparalleled Portability and Protection For Patient Data*, Heartlab, printed from website www.heartlab.com/benefits_portability.htm on Jan. 27, 2004, (1 pg.).
*Ease of Use*, Heartlab, printed from website www.heartlab.com/benefits_simplicity.htm on Jan. 27, 2004, (1 pg.).
*System Flexibility For Long-Term Protection of Your Technology Investment*, Heartlab, printed from website www.heartlab.com/benefits_flexibility.htm on Jan. 27, 2004, (1 pg.).
*Encompass: Not just a system—a solution*, Heartlab, printed from website www.heartlab.com/products_0.htm on Jan. 27, 2004, (11 pgs.).
*St. Francis Medical Center*, Heartlab, printed from website www.heartlab.com/casestudies_3.htm on Jan. 27, 2004, (4 pgs.).
*University of Chicago and Heartlab Forge Clinical Cooperation Agreement for Encompass System Enhancements*, Heartlab, dated Aug. 21, 2001, (2 pgs.).
*Actuality Systems—Photographs*, Actuality Systems, copyright date: 2001, printed from website www.actuality-systems.com/photographs.php3 on Nov. 25, 2003, (3 pgs.).
*Welcome to SeeReal Technologies GmbH*, SeeReal Technologies, copyright date: 2003, printed from website www.seereal.com/default.en.htm on Feb. 17, 2004, (1 pg.).

*Autostereoscopic 3D Display in Laparoscopic Surgery*, University of Cambridge, Cambridge, United Kingdom, presented at CAR '95, Berlin, Jun. 21-24, 1995, printed from website www.cl.cam.ac.uk/users/nad/car95_paper.html on Feb. 16, 2004, (1 pg.).

*SeeReal 3D Displays—"C" Display*, SeeReal Technologies, copyright date: 2003, printed from website www.seereal.com/EN/products.en.htm on Feb. 16, 2004, (1 pg.).

*SeeReal Technologies—Areas of Use*, SeeReal Technologies, copyright date: 2003, printed from website www.seereal.com/EN/use.en.htm on Feb. 16, 2004, (1 pg.).

K. Radermacher, C.V. Pichler, S. Fischer, G. Rau, *3D-Visualisation in Surgery*, Helmholtz-Institute for Biomedical Engineering, Aachen University of Technology, Aachen, 1998, (6 pgs.).

*Siemens and X3D unveil the first Extreme 3D Display for medical application*, Virtual Medical Worlds Monthly, dated Oct. 22, 2003, printed from website www.hoise.com/vmw/03/articles/vmw?LV-VM-11-03-27.html on Feb. 16, 2004, (2 pgs.).

*Siemens unveils the first Extreme 3D Display for medical application*, Siemens AG, dated Oct. 22, 2003, printed from website http://siemens.com/index.jsp?sdc_p=d1047890po1105117fcls4mn1031561u&... on Feb. 16, 2004, (2 pgs.).

Gregg Favalora and Cameron Lewis, *Spatial 3D: The End of Flat-Screen Thinking*, Actuality Systems, Inc., Jul. 2003, (9 pgs.).

CALYSTO™ for Cardiology—Overview, Witt Biomedical, printed from website www.wittbiomedical.com/products.cfm?secID=1 on Apr. 1, 2004, 1 page.

Astrom, M. et al., Least Squares VCG Loop Alignment, 4 Pages.

Astrom M. et al., Vectorcardiographic Loop Alignment and the Measurement of Morphologic Beat-to-Beat Variability in Noisy Signals, IEEE Transactions on Biomedical Engineering, vol. 47, No. 4, Apr. 2000, pp. 497-506.

Astrom M., Vectorcardiographic Loop Alignment in Ischemia Monitoring, Licentiate in Engineering Thesis, Apr. 2000, 75 Pages.

* cited by examiner

US 7,966,058 B2

SYSTEM AND METHOD FOR REGISTERING AN IMAGE WITH A REPRESENTATION OF A PROBE

BACKGROUND

The present description relates generally to systems and methods for registering or aligning an image with a representation of a probe. In particular, the present description relates to improved systems and methods for registering a cardiac image with a representation of a probe.

Electrophysiology (EP) studies can be used to diagnose and/or treat a number of serious heart problems. One type of heart problem that can be diagnosed and/or treated by conducting an EP study is cardiac arrhythmias. Cardiac arrhythmias can generally be referred to as abnormal heart rhythms such as tachycardias, bradycardias, etc. Left untreated, an arrhythmia presents a serious health risk to an individual.

In a typical EP study, a catheter (e.g., electrode catheter, balloon catheter, etc.) is inserted into a vein or artery (e.g., in the groin, etc.) and guided to the interior of the heart. Once inside the heart, the catheter is contacted with the endocardium at multiple locations. At each location, the position of the catheter and the electrical properties of the endocardium can be measured. The attending physician can use this data to assist in locating the origin of a cardiac arrhythmia. The results of the EP study may lead to further treatment, such as the implantation of a pacemaker or implantable cardioverter defibrillator, or a prescription for antiarrhythmic medications. Oftentimes, however, the physician ablates (e.g., RF ablation, etc.) the area of the heart causing the arrhythmia immediately after diagnosing the problem. Generally, ablating an area of the heart renders electrically inoperative thus removing stray impulses and restoring the heart's normal electrical activity.

In some EP studies, physicians also refer to a three dimensional (3D) image of the heart such as images obtained using computerized tomography (CT), magnetic resonance (MR), ultrasound, etc. Unfortunately, the image is typically not registered with the location of the catheter used in the EP study. Thus, although the physician can refer to the image, the location of the catheter relative to the image is unknown. Accordingly, it would be desirable to provide an improved system and method for registering a representation of a catheter (or, broadly speaking, a probe) with an image.

SUMMARY

One embodiment relates to a method comprising acquiring an image of or pertaining to a heart and registering a representation of a probe which is in or adjacent to the heart with the image using a heart vector of the heart.

Another embodiment relates to a method comprising: acquiring an image of or pertaining to a heart, acquiring a first data set pertaining to one or more locations of a heart vector of the heart, the first data set being spatially correlated with the image, acquiring a second data set pertaining to one or more locations of the heart vector of the heart, registering a representation of the probe with the image by registering the location of the heart vector from the first data set with the location of the heart vector from the second data set.

Another embodiment relates to a method comprising acquiring an image of or pertaining to a heart and adjusting the size and/or position of the image using a heart vector of the heart.

Another embodiment relates to a system which comprises a processor, memory, and a display. The processor is configured to be communicatively coupled to a probe. The probe is configured to be located in or adjacent to a heart. The memory is configured to store an image of at least a portion of the heart, a first data set pertaining to one or more locations of a heart vector of the heart, and a second data set pertaining to one or more locations of the heart vector of the heart. The first data set is spatially correlated with the image. The display is configured to display the image and a representation of the probe. The image is registered with the representation of the probe by registering the heart vector from the first data set with the heart vector from the second data set.

DETAILED DESCRIPTION

The present description is generally provided in the context of registering (spatially, temporally, etc.) one or more images (e.g., 3D images, 4D images, volume rendered images, images obtained using CT, MR, and/or ultrasound, etc.) of an organ or structure inside a body with one or more representations of one or more probes (e.g., catheter, instrument, etc.) which are also inside the body. Although, the present description is provided primarily in the context of registering one or more images of the heart with a representation of a probe which is inside the heart, it should be understood that the systems and methods described and claimed herein may also be used in other contexts such as registering one or more images of other organs or structures (e.g., brain, liver, etc.) of a human or, broadly speaking, animal body, with the representation of a probe which is inside the human or animal body. Accordingly, the systems and methods described herein are widely applicable in a number of other areas beyond what is described in detail herein. Also, it should be understood that although a single image is oftentimes registered to a single representation of a probe, one or more images may be registered with one or more representations of one or more probes. It should also be understood that a particular example or embodiment described herein may be combined with one or more other examples or embodiments also described herein to form various additional embodiments as would be recognized by those of ordinary skill. Accordingly, the systems and methods described herein may encompass various embodiments and permutations as may be appropriate and/or recognized by those of ordinary skill.

Figure 1:
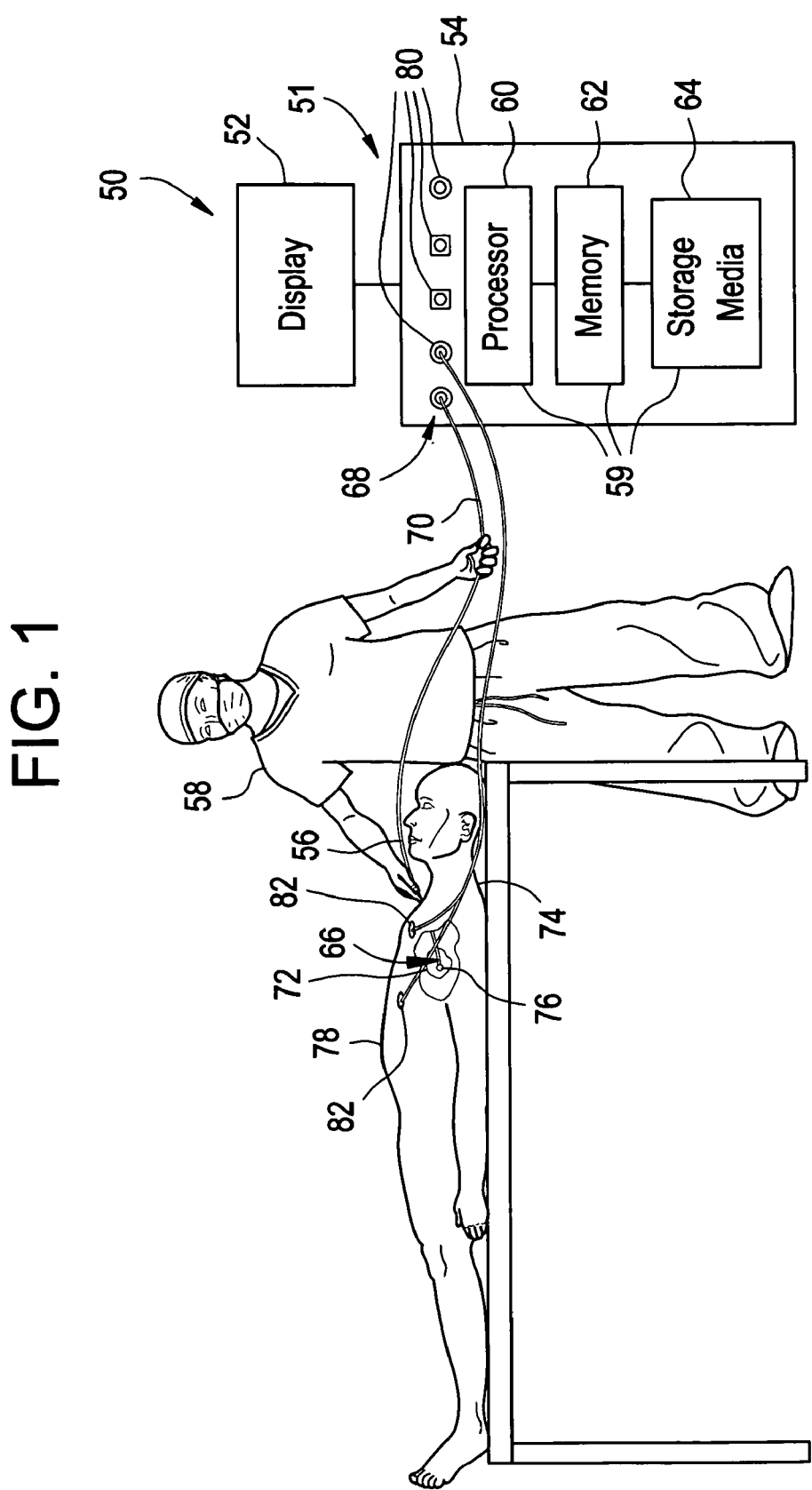
FIG. 1 is a system for registering a representation of a probe with an image according to one embodiment.

Referring to FIG. 1, one embodiment of a system 50 is shown. System 50 includes a console or computer 51 and a probe 56. System 50, broadly described, may be used to register an image with a representation of a probe 56. The term "representation" as used herein should be given its ordinary and accustomed meaning. However, regardless of its ordinary and accustomed meaning, the term "representation" should not be construed to require the representation to be in any way similar in size, shape, etc. (although they may be similar in size, shape, etc.) as the thing being represented (e.g., a square is used to represent probe 56 even though probe 56 is not the shape or size of a square). In particular, system 50 may be used to spatially and/or temporally register an image with the representation of probe 56.

System 50 may be a wide variety of systems used for an equally wide variety of uses. For example, in one embodiment, system 50 may be any system that is configured to use a probe to measure, monitor, diagnose, manipulate, or otherwise provide information about an organ or structure inside the body. In another embodiment, system 50 may be an EP monitoring system that is configured to use a probe to purposefully alter or provide information regarding the electrical activity of an organ or structure inside the body. In another embodiment, system 50 may be a cardiac EP monitoring system. In general, the cardiac EP monitoring system is configured to provide information about or purposefully alter the electrical activity of a heart using a probe which is in or adjacent to the heart.

As shown in FIG. 1, probe 56 and display 52 are communicatively coupled to computer components 59 in cabinet 54. Information sensed by probe 56 may be communicated to computer components 59. Information from computer components 59 may then be communicated to display 52 where it is displayed to a nearby person 58 (e.g., attending physician, nurse, technician, etc.). The configuration shown in FIG. 1 is only one of many suitable configurations. For example, in another embodiment, probe 56 may be communicatively coupled directly to display 52. In this embodiment, display 52 may be configured to display the information provided by probe 56 without the information being communicated through cabinet 54 (e.g., display 52 comprises the necessary computer components 59 to receive information from probe 56). In another embodiment, display 52 may be combined with cabinet 54 so that the functions generally performed by computer components 59 in cabinet 54 and display 52 are performed by the combined unit (e.g., display 52 comprises all of computer components 59). In another embodiment, console 51 may include two or more displays 52. The displays may be used to display multiple images or other types of information (e.g., electrocardiogram (ECG) signals, etc.) In one embodiment, display 52 may be configured to be in a location that is convenient for person 58 to view (e.g., at height of person 58's eyes as person 58 is standing, etc.) as person 58 moves probe 56.

System 50 may also be configured to include additional components and systems. For example, system 50 may comprise a printer. System 50 may also be configured as part of a network of computers (e.g., wireless, cabled, secure network, etc.) or as a stand-alone system. In one embodiment, system 50 may comprise an ECG monitoring system. The ECG monitoring system may be a conventional twelve lead ECG monitoring system. In other embodiments, the ECG monitoring system may include any suitable and/or desirable configuration of leads, etc. to provide the information necessary for the particular use of system 50. In another embodiment, system 50 may comprise a system to monitor the blood pressure of patient 74. This may be a conventional blood pressure monitoring system or may be a system that monitors the blood pressure using a transducer placed on or adjacent to a vein or artery. In another embodiment, system 50 may comprise a localization system, which may be used to determine the location of probe 56. In short, there are a number of conventional systems and components recognized by those of ordinary skill that may also be included as part of system 50.

Computer components 59 in cabinet 54, shown in FIG. 1, comprise a processor 60, memory 62, storage media 64, and one or more input devices (e.g., mouse, keyboard, etc.). Computer components 59 are configured to receive information from probe 56, process the information, and provide output using display 52. The information provided to computer components 59 may be continually stored (i.e., all information is stored as it is received) or intermittently stored (i.e., periodic samples of the information are stored) using storage media 64 (e.g., optical storage disk (e.g., CD, DVD, etc.), high performance magneto optical disk, magnetic disk, etc.) for later retrieval. In general, storage media 64 differs from memory 62 in that storage media 64 is configured to maintain the information even when storage media 64 is not provided with power. In contrast, memory 62 typically does not maintain the information when the power is off.

In one embodiment, console 51 is a desktop computer. In another embodiment, console 51 may be configured to include input locations 80 on cabinet 54 or display 52 that are configured to receive additional information pertaining to patient 74. For example, in one embodiment, input locations 80 may include one or more input locations configured to receive input from leads 82 (e.g., ECG leads, etc.).

Probe 56 comprises a distal end 66, a proximal end 68, and a probe body 70. In general, probe 56 may be located in or adjacent to a heart 72 (shown in FIG. 1 in a cross-sectional view to expose distal end 66 of probe 56) of patient 74. In one embodiment, distal end 66 may include one or more sensors 76, which are configured to sense the electrical properties (e.g., electrical potential at one or more locations of the endocardium, activation times, etc.) of heart 72. The electrical properties may then be communicated back to console 51 and displayed on display 52. In an exemplary embodiment, probe 56 may comprise a plurality of sensors configured to sense the electrical properties of heart 72 (e.g., probe 56 is a balloon catheter, etc.). In another embodiment, multiple probes 56 may be used that each comprise one or more sensors configured to sense the electrical properties of heart 72.

Probe 56 may be any number of suitable probes having a variety of configurations. For example, probe 56 may include a lumen in which wires may be placed to communicate information from sensors 76 back to console 51 and to transmit an ablation charge from console 51 to distal end 66 to correct the electrical pathways in heart 72. Of course, the lumen may also be used to allow fluid to flow through probe 56.

In another embodiment, a localization system, included as part of system 50, may be used to determine the location of one or more portions of distal end 66 of probe 56. This may useful to move probe 56 back to an earlier location. Any suitable localization system may be used as would be recognized by those of ordinary skill. For example, the location of distal end 66 of probe 56 may be determined using one or more transmitters and/or receivers that are located outside the body of patient 74 (typically at least three transmitters and/or receivers are used). In this example, the transmitters and/or receivers may be configured to send and/or receive signals to and/or from distal end 66. These signals may be used to determine the location of distal end 66. In one embodiment, the transmitters and/or receivers may be incorporated into one or more leads 82 positioned on skin surface 78 of patient 74. In another embodiment, the transmitters and/or receivers may be positioned so as not to be in contact with patient 74. In another embodiment, leads 82 may be used to determine the location of distal end 66 of probe 56 by sending a signal that is useful in determining the impedance of probe 56, which may be used to determine the location of probe 56. In another embodiment, the localization system may be configured to determine the location of multiple sensors 76 on distal end 66 of probe 56. Also, as described in further detail below, the location of sensors 76 may also be used in registering the representation of probe 56 with an image on display 52.

Display 52, shown in FIG. 1, is configured to provide output to a user in the form of information, which may include alphanumeric (e.g., text, numbers, etc.) output, graphical image output, etc. In one embodiment, display 52 may be configured to also receive input from a user (e.g., touch screen, buttons located adjacent to the screen portion of display 52, etc.). Display 52 may be any number of suitable displays in a number of suitable configurations. For example, display 52 may be a liquid crystal display, flat screen display, SVGA display, VGA display, etc.

In one embodiment, display 52 may be configured to display one or more images of an organ or structure inside the body (e.g., a heart). Desirably, display 52 may be configured to display images acquired using CT, MR, and/or ultrasound. These images may also be two-dimensional, three-dimensional, or four-dimensional. Also, in many instances, the images are generated from data processed by a computer (CT, MR, ultrasound, etc.). Typically, in embodiments where the image is a CT or MR image, the images are input into system 50 prior to probe 56 being inserted into patient 74 or before a procedure (e.g., an electrophysiology monitoring procedure) is initiated.

Display 52 may also be configured to display one or more representations of one or more probes 56 and the information provided by probes 56. For example, in one embodiment, display 52 may be configured to display a representation of probe 56. In another embodiment, display 52 may be configured to display representations of sensors 76 which are on probe 56. In another embodiment, display 52 may be configured to display the electrical properties of the organ or structure which are sensed by sensors 76. In another embodiment, display 52 may be configured to display markers showing one or more locations where the electrical properties have been sensed. In one embodiment, each marker may display an abbreviated amount of information regarding the electrical properties. When a user selects one of the markers, the user is shown a greater amount of information relating to the electrical properties. In embodiments where the organ or structure comprises heart 72, these markers may be color coded based on the activation times at the various locations inside heart 72 (e.g., red is for early activation times and blue is for late activation times). By displaying a number of markers on display 52, the user can readily observe the electrical properties of various areas of heart 72. Any suitable marker or identifier may be used to represent probe 56 on display 52. For example, in one embodiment, probe 56 may be displayed as a line with a series of points corresponding to sensors 76. The line segments connecting the points represent the portion of probe 56 where there are no sensors. Of course, probe 56 may be shown or represented on display 52 in any of a number of other suitable ways as well.

Of course, display 52 may be configured to display one or more images in conjunction with one or more of the representations of probe 56 and the information provided by probe 56. For example, in one embodiment, display 52 may be configured to simultaneously display an image of heart 72, a representation of probe 56, and a map of the electrical properties of heart 72, all of which are registered to each other. In another embodiment, the image and the representation of probe 56 may be spatially registered. In a further embodiment, the map may be a three-dimensional map of the electrical properties. Of course, in addition to the embodiments specifically described, display 52 may be configured to display any suitable combination of the image, the representation of probe 56, and other information (e.g., electrical properties of heart 72, etc.), of which at least two of these are registered according to the embodiments described later. In one embodiment, system 50 may be configured to display an image of heart 72 that is registered with probe 56 on display 52. In this manner, person 58 is able to simply look at display 52 to determine the location of probe 56 inside heart 72. Person 58 may then adjust and manipulate probe 56 accordingly.

In one embodiment, display 52 may be configured to overlay the image, the representation of probe 56, and any other information (e.g., electrical properties of heart 72). This may be advantageous to provide person 58, who is viewing display 52, the ability to quickly and easily recognize the information presented on display 52. Of course, other suitable ways of displaying the image, the representation of probe 56, and any other information may also be used.

The representation of probe 56 may be registered with the image of an organ or structure of a body (e.g., a heart, etc.) spatially and/or temporally (e.g., to substantially the same point of a bodily cycle such as a cardiac cycle, etc.). A number of embodiments are described that may be used to register the representation of probe 56 with the image both spatially and temporally.

In one embodiment, the representation of probe 56 may be registered with the image using one or more features (e.g., physical features) of the organ or structure in the body. For example, when the organ or structure comprises heart 72, the features may include valves, atrial appendages, scar tissue, etc.

Figure 2:
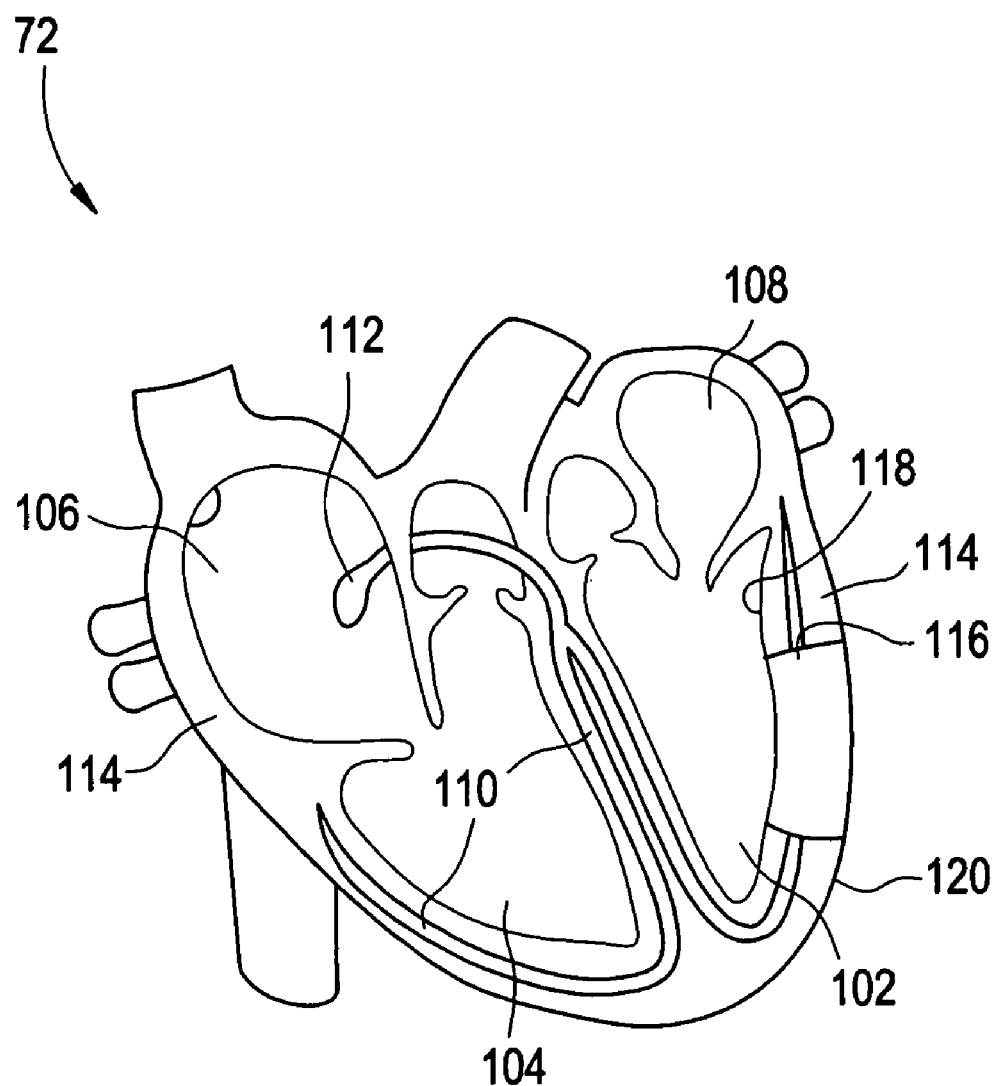
FIG. 2 is a cross-sectional view of a heart according to one embodiment.

Referring to FIG. 2, a cross-sectional view of heart 72 is shown comprising a feature 116. Heart 72 also includes a left ventricle 102, a right ventricle 104, a right atrium 106, and a left atrium 108. Also shown in FIG. 2 are electrical pathways 110 and sinoatrial (S-A) node 112. The pumping action of heart 72 begins when an electrical pulse, originating at S-A node 112, travels through heart 72. As the pulse travels, walls 114 of heart 72 contract in a progressive manner, thus moving blood through the various chambers of heart 72 and on through the circulatory system. When heart 72 is at rest, the muscle is polarized. The pulse originates at S-A node 112 when the heart tissue begins to depolarize. This depolarization wave spreads (and thus so does the pulse) along pathways 110 throughout the rest of heart 72.

Feature 116, shown in FIG. 2, is, in this example, scar tissue, but may be a number of other features that are suitable for use in registering the representation of probe 56 and the image as mentioned previously. For example, in one embodiment, feature 116 may be any feature that is identifiable by both it electrical properties (e.g., electrical potential as measured in an EP study, etc.) and other properties (e.g., color, size, orientation, density, etc.) which can be observed visually on images derived from a variety of imaging modalities (e.g., CT, MR, ultrasound, etc.). Also, it should be understood, that although feature 116 is shown as extending from interior surface 118 of heart 72 to exterior surface 120 of heart 72, feature 116 does not have to extend through wall 114. Rather, feature 116 may extend from interior surface 118 outward into one of chambers 102, 104, 106, and 108 of heart 72, or may simply be a small amount of scar tissue on interior surface 118 that does not extend entirely through wall 114. In one embodiment, feature 116 may be a feature that was created and/or identified previously. For example, feature 116 may be electrically inactive and/or scarred tissue from a previous ablation or surgery, etc.

Figure 3:
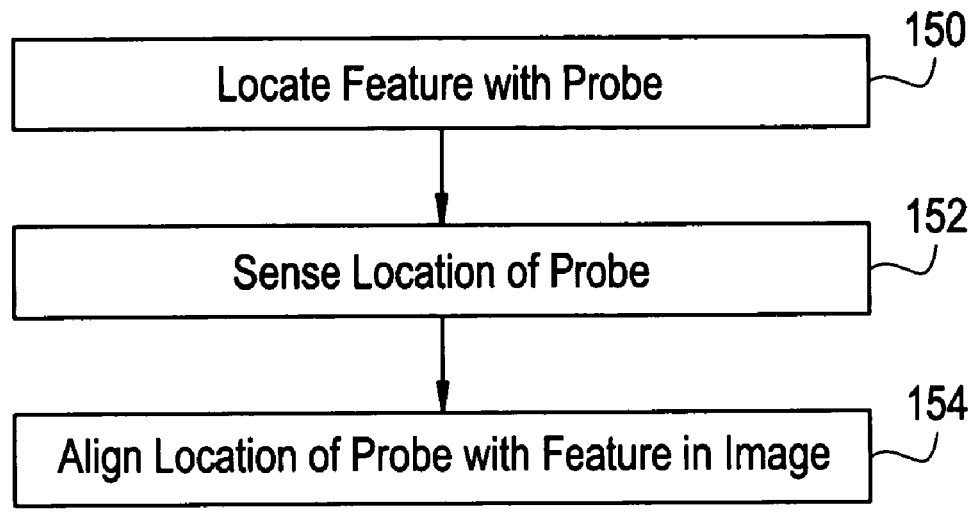
FIG. 3 shows a block diagram of a method for registering a representation of a probe with an image according to one embodiment.

Referring to FIG. 3, a diagram is shown of a method for registering a representation of probe 56 with an image using feature 116. At step 152, probe 56 is used to locate feature 116 on interior surface 118 of heart 72. In one embodiment, this is done by person 58 who moves probe 56 until feature 116 is located based on its electrical properties (e.g., scar tissue having zero conductivity, etc.). Typically, probe 56, and specifically, sensor 76 contact feature 116 during step 152. Referring back to FIG. 3, once feature 116 has been located, the location of probe 56 is sensed at step 152. The location is stored in system 50 and/or displayed on display 52. Typically, the location of probe 56 is sensed using a localization system, which may be included as part of system 50.

In one embodiment, at step 150, probe 56 may be able to locate feature 116 by sampling one location on interior surface 118 of heart 72. For example, in situations where feature 116 is similar in size to sensor 76 then feature 116 may be located by sampling a single location. However, in other embodiments, it may be desirable to sample multiple locations to determine the boundaries of feature 116.

Figure 4:
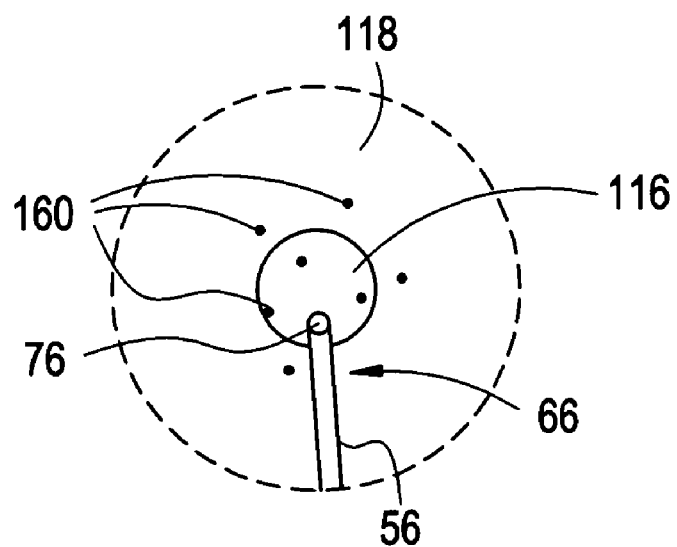
FIG. 4 shows a cross-section view of a portion of heart according to another embodiment.

For example, FIG. 4 shows a cross-sectional view of heart 72 with distal end 66 of probe 56 located adjacent feature, 116. In this example, distal end 66 includes at least one sensor 76 which may be used to sense electrical properties as well as determine the location of probe 56. Points 160 refer to locations where sensor 76 sensed the electrical properties of interior surface 118 of heart 72. Feature 116 is shown as being circular, however, it should be understood that feature 116 may be any of a number of shapes and sizes. As shown in FIG. 4, probe 56 measures the electrical properties at points 160 to determine the boundaries of feature 116. Accordingly, depending on the size and shape of feature 116 it may be necessary to measure the electrical properties of multiple points 160 before registering the location of probe 56 with the image.

Once the boundaries of feature 116 have been located using probe 56, then the shape and size of feature 116 located by probe 56 may be compared to features 116 shown in the image. If there is a feature in the image that is similar in shape and size to feature 116 located using probe 56 then it is likely they are a match, especially if there is only one feature in the image that is of similar size and shape. If they match, then the representations of probe 56 displayed on display 52 that correspond to points 160 can be registered with the image. If, however, there are multiple features 116 in the image that may be the same shape and size as feature 116 located using probe 56, then it may be desirable to continue to locate other features 116. Once the location, shape, and size of another feature 116 has been determined using probe 56 then the two features located using probe 56 may be registered to features 116 in the image. Because the locations of the two features 116 are known relative to each other, features 116 that have a similar spatial relationship may be located in the image.

Referring back to FIG. 3, once the location of feature 116 has been determined, the representation of probe 56 is registered with feature 116 in the image at step 154. In one embodiment, this may be done by a user such as person 58 who visually locates feature 116 in the image and registers the representation of probe 56 to feature 116 displayed in the image. For example, system 50 may be configured so that the user can select the representation of probe 56 on display 52 and drag and drop the representation on feature 116 shown in the image. The location of probe 56 and the image are now registered at that feature. Of course, other methods may be used to register the location of probe 56 with feature 116 in the image. Once one representation of probe 56 has been registered with the image, steps 150-154 may be repeated for additional features 116 thereby registering the image with a number of the representation of probe 56. In an exemplary embodiment, it is desirable to register the image with at least three representation of probe 56.

In another embodiment, step 154 may be performed entirely by system 50. In this embodiment, system 50 may be configured to register the representation of probe 56 with the image using at least one feature 116, or, desirably, using two, three, or more features 116. Using system 50 may be desirable because the images are registered in a faster and more consistent (e.g., registration procedures use a common algorithm or set of algorithms to register the images) manner. System 50 may be configured to register the image and the representation of probe 56 in a similar manner to the method a user would perform except that system 50 uses software to perform the similar procedures. In one embodiment, the software may be configured to provide instructions to determine the location of multiple features 116 in the image. Once the location of feature 116 has been determined, system 50 may, using the software, begin to search for the corresponding feature 116 in the image. This may be particularly useful once probe 56 has located two, three, or more features. System 50 may use the software to compare the locations of the features 116 relative to each other to find corresponding features 116 in the image that have similar spatial relationships. Once features 116 in the image have been located, then the representations of probe 56 corresponding to features 116 may be registered with the image.

In one embodiment, the software (e.g., computer readable instructions) may be configured to locate one or more features 116 in the image by sensing the electrical properties of heart 72 at various locations (the user is typically still responsible to move probe 56 in heart 72) and determining whether the electrical properties at a particular location are abnormal (e.g., location of scar tissue is non-conducting, potential measured a particular location is lower or higher than normal, etc.). System 50 may comprise a database of electrophysiological measurements taken previously from patient 74 or a group of other patients, which can then be compared with the present measurements to determined if they are abnormal.

In another embodiment of step 150, feature 116 may be identified using a combination of software and visual perception by person 58 or any other suitable person. For example, system 50 may comprise software that preliminarily locates feature 116 (or a plurality of features 116) in the image and displays the image showing feature 116 selected (e.g., circled, highlighted, etc.). The person can then view the image on display 52 and judge whether the software has accurately located feature 116. If feature 116 is not accurately located, then person 58, using a user interface, can manually locate feature 116 or slightly adjust the selection of feature 116 provided by the computer. Once feature 116 is located in the image, then the image may be registered to the representation of probe 56.

Figure 5:
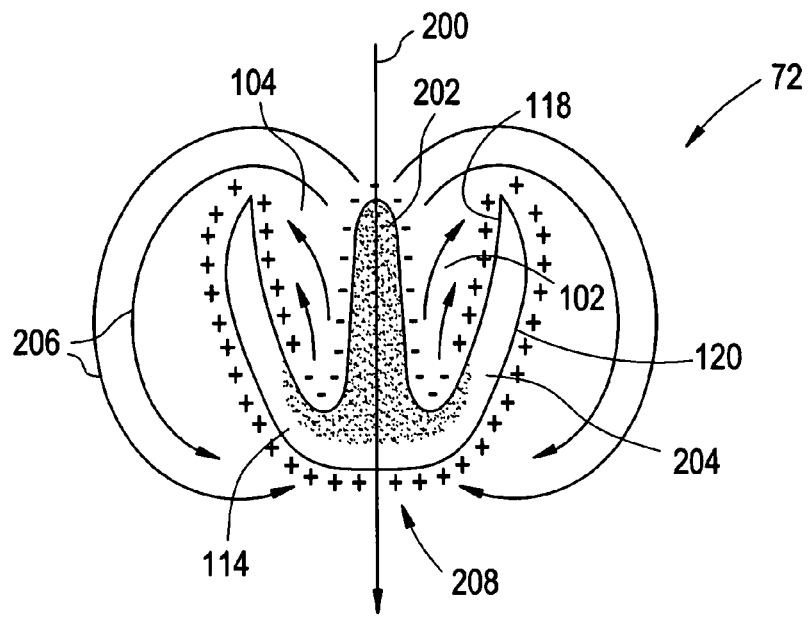
FIG. 5 shows another cross-sectional view of a portion of a heart according to another embodiment.

In another embodiment, a representation of probe 56 is registered with an image of heart 72 using a heart vector 200 (e.g., electrical heart vector or electrical axis, etc.). Referring to FIG. 5, a portion of heart 72 is shown. The portion of heart 72 generally shows walls 114 of ventricles 102 and 104. Electrical currents flow in the ventricles between depolarized areas 202 (i.e., the shaded areas in FIG. 5) inside the heart and polarized areas 204 on the outside of the heart as indicated by arrows 206. Currents also flow inside heart 72 from depolarized areas 202 toward polarized areas 204. Even though a small amount of current flows upward inside heart 72, a considerably greater quantity flows downward toward an apex 208 of heart 72. All of the vector currents in heart 72 at any given instant in time may be summed to create heart vector 200. In FIG. 5, heart vector 200 represents the summation of all of the currents in heart 72 at a particular instant in time. In addition to showing the direction of the sum of the currents in heart 72, the length of heart vector 200 is proportional to the quantity of the current. Accordingly, heart vector 200 increases in length when there is more current flowing in heart 72.

Figure 6:
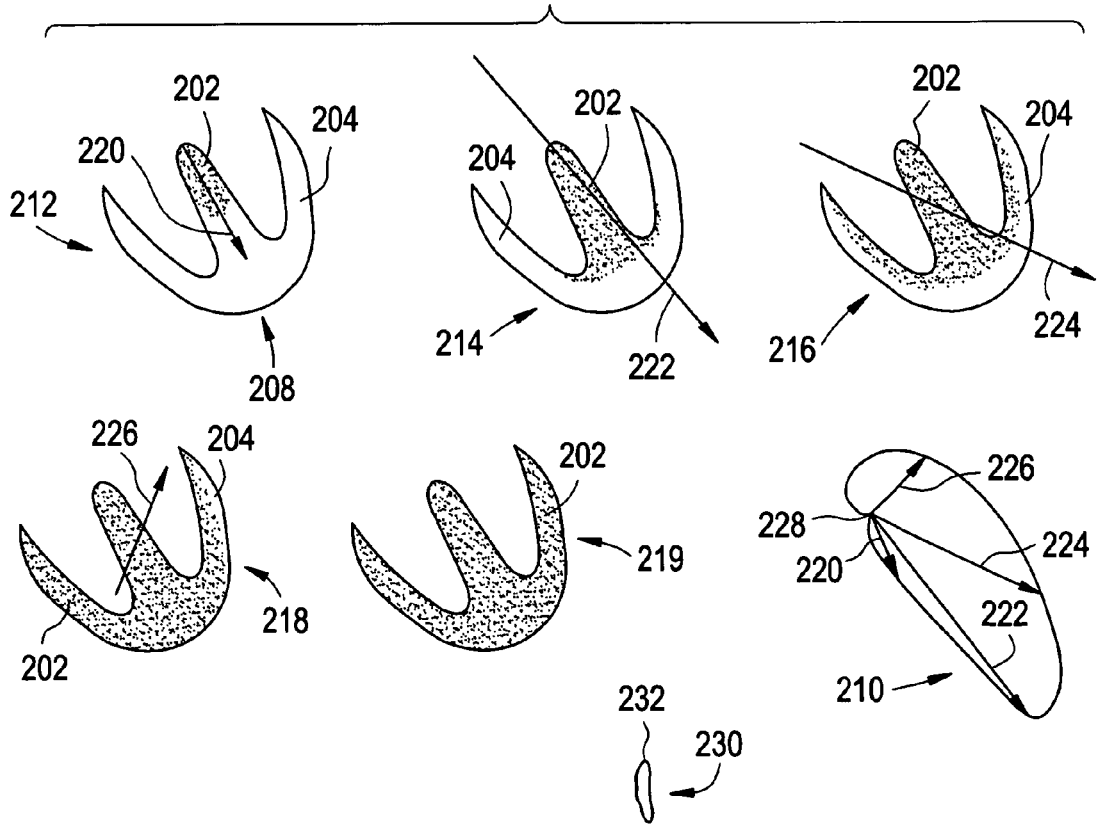
FIG. 6 shows a plurality of heart vectors and vector loops according to another embodiment.

Referring to FIG. 6, a vector loop 210 is shown of heart vector 200 at various times in the QRS portion of a cardiac cycle. FIG. 6 also shows various stages 212, 214, 216, 218, and 219 of the depolarization of heart 72 in the QRS portion of the cardiac cycle. Stages 212, 214, 216, and 218 correspond to heart vectors 220, 222, 224, and 226, respectively. Stage 219 corresponds to when heart 72 is completely depolarized and, accordingly, there is no current or a very small amount of current flowing.

Referring to FIG. 6, heart vectors 220, 222, 224, and 226 show that heart vector 200 changes in both quantity and direction as the cardiac cycle proceeds. As previously discussed, the heart vector increases and decreases in length because the current flow in heart 72 is increasing and decreasing. Heart vector 200 changes direction in the cardiac cycle because of changes in the average direction of current flow around heart 72. As shown in vector loop 210, which represents heart vector 200 during the QRS portion of the cardiac cycle, point 228 corresponds to the location where there is no or very little current flow in heart 72. As heart 72 first becomes depolarized, shown in stage 212, heart vector 220 extends downward toward apex 208 of heart 72 and is relatively weak. As more of heart 72 becomes depolarized, shown in stage 214, heart vector 222 becomes stronger and begins to swing slightly to one side. At stage 216, heart vector 224 is still relatively strong, but not quite as strong as heart vector 222. However, at stage 216, heart vector 224 begins to swing even further to one side (shown in FIG. 6 as a counterclockwise rotation from each progressive stage). Also, at stage 216 much of the heart has become depolarized. At stage 218, most of heart 72 has become depolarized and heart vector 226 is smaller than heart vector 224. Finally, at stage 219, heart 72 has become completely depolarized. Although FIG. 6 shows vector loop 210 being two-dimensional, it should be understood that vector loop 210 is often three-dimensional and that a two-dimensional illustration is provided for illustration purposes only. Accordingly, vector loop 210 may be represented using a three-dimensional coordinate system (e.g., rectangular coordinates, spherical coordinates, etc.).

In addition to vector loop 210 formed during the QRS portion of the cardiac cycle, other vector loops may be formed during other portions (e.g., P portion, T portion, etc.) of the cardiac cycle. For example, as shown in FIG. 6, vector loop 230 is formed during the depolarization that occurs in the T portion of the cardiac cycle. Also, a small vector loop (not shown) may be formed during the P portion of the cardiac cycle. As shown in FIG. 6, vector loop 210 is quite a bit larger than vector loop 230.

Figure 7:
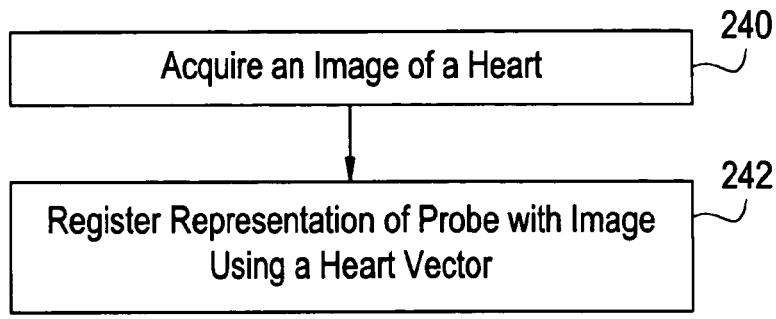
FIG. 7 shows a method for registering a representation of a probe with an image according to another embodiment.

Referring to FIG. 7, one embodiment of a method for registering a representation of probe 56 with an image using heart vector 200 is shown. At step 240, an image of heart 72 is acquired. The image may be any of the number of images described previously. In one embodiment, the image is a three-dimensional CT image. In one embodiment, a first heart vector data set is spatially correlated with the image. This may be done by acquiring the first heart vector data set at the same time or shortly before or after the image is acquired. For example, as the image is being acquired by, for example, CT imaging equipment, the first heart vector data set may be simultaneously acquired and the location of heart vector 200 or multiple locations of heart vector 200 in at least a portion of a cardiac cycle (which may be represented by vector loops 210 or 230) are correlated to the location of heart 72 in the image. In one embodiment, the first heart vector data set is acquired for the QRS portion of multiple cardiac cycles. In another embodiment, first heart vector data set comprises at least ten seconds of data from selected portions of a cardiac cycle or from the entire cardiac cycle. The ten seconds of data may then be averaged to provide the average location of heart vector 200 for one or more portions (e.g., QRS portion, T portion, etc.) of the cardiac cycle (e.g., enough locations of heart vector 200 may be acquired and averaged to provide what may be considered an average of vector loop 210). In another embodiment, data is taken for at least ten seconds, twenty seconds, thirty seconds, or the majority of the time that it takes to acquire the image of the location of heart vector 200 for one or more portions of the cardiac cycle. Again, the data is averaged to provide the average location of heart vector 200. In one embodiment, the data is acquired by sampling the location of heart vector 200 at least five hundred to one thousand times per second.

In one embodiment, the first heart vector data set is acquired using a conventional twelve lead ECG system. Of course, in other embodiments, various lead systems other than a twelve lead ECG system may be used to acquire data pertaining to the location of heart vector 200. As mentioned above, the location of heart 72 in the image may be correlated to one or more locations of heart vector 200 acquired in the first heart vector data set using the location of ECG leads 82. The location of ECG leads 82 are known relative to the location of heart vector 200 and relative to the image. Accordingly, using ECG leads 82, the location of heart vector 200, acquired in connection with the first heart vector data set, may be correlated with the location of heart 72 in the image.

At step 242, the representation of probe 56 is registered with the image using heart vector 200. Typically, but not always, step 242 is performed after the image has been acquired and probe 56 has been located in the body of patient 74 (e.g., image is acquired in radiology lab, patient 74 is transferred from radiology lab to electrophysiology lab, probe 56 is inserted into patient 74, representation of probe 56 is registered with the image). Also, it should be noted that in many instances probe 56 is inserted into the body of patient 74 after the image is acquired.

In one embodiment, the location of probe 56 is determined relative to one or more locations of heart vector 200 (e.g., location of probe 56 is determined relative to multiple locations of heart vector 200 such as the multiple locations shown by vector loop 210). In another embodiment, the location of probe 56 is determined relative to the location of leads 82, and, thus, also relative to the location of heart vector 200. A localization system, as discussed previously, may be used to determine the location of probe 56 in relation to leads 82. Once the location of probe 56 relative to heart vector 200 has been determined, then the representation of probe 56 may be registered with the image using one or more locations of heart vector 200.

In one embodiment, registering the representation of probe 56 and the image is accomplished by registering the first heart vector data set with a second heart vector data set. In general, the second heart vector data set is correlated to the location of probe 56, while the first heart vector data set is correlated to the location of heart 72 in the image. Therefore, by registering the two data sets with each other the representation of probe 56 may be registered with the image.

Samples of the location of heart vector 200 may be acquired in a manner similar to that described with respect to the first heart vector data set. In one embodiment, the second heart vector data set is acquired while probe 56 is inside the body of patient 74. For example, the second heart vector data set may be acquired when patient 74 is in the electrophysiology lab and probe 56 has just been inserted into the body of patient 74. In another embodiment, the second heart vector data set may be acquired before probe 56 is inserted into patient 74. In another embodiment, the second heart vector data set may be acquired at the beginning of an EP procedure or shortly after probe 56 has been inserted into the body of patient 74. Once a sufficient number of samples have been acquired, the first and second heart vector data sets are registered with each other, thus registering the representation of probe 56 with the image. After the representation of probe 56 has been registered with the image, then the EP procedure is continued without registering the representation of probe 56 with the image again.

In another embodiment, the representation of probe 56 may be registered with the image periodically (e.g., every hour, half hour, ten minutes, etc.) during the time that probe 56 is located in the body. In another embodiment, the representation of probe 56 may be continuously or substantially continuously (e.g., once every cardiac cycle, once every third cardiac cycle, etc.) registered with the image. In one embodiment, the second heart vector data set may be a revolving data set. For example, the second heart vector data set may be configured to only use data acquired since the last time the representation of probe 56 was registered with the image (e.g., if registration is occurring once every cardiac cycle then only data from one cardiac cycle is registered with the first heart vector data set). Of course, even if the second heart vector data set is a revolving data set, the data may still be averaged over the revolving time period (e.g., registration occurs every ten minutes and the second heart vector data set is averaged for a portion or all of a cardiac cycle from the last five minutes, or two minutes, etc.). In acquiring the first and second heart vector data sets, ectopic beats may be excluded from the averaging process. Also, beats from which heart vector data sets are acquired are generated from the same type of rhythm (e.g., sinus rhythm or other atrial rhythms). In another embodiment, the second heart vector data set may include data used to previously register the representation of probe 56 and the image. For example, if the representation of probe 56 and the image are registered every three cardiac cycles, then the second heart vector data set may include data used previously. In another embodiment, system 50 may be configured to determine whether the cardiac cycle of patient 74 has changed significantly, at which point the second heart vector data set revolves so that older data is no longer used to register the representation of probe 56 with the image.

The first and second heart vector data sets may be registered to each other in a number of ways. For example, in one embodiment, a least squares method may be used to register the two data sets. In this embodiment, the data sets both comprise data from the QRS portion of the cardiac cycle as shown by vector loop 210. The process of registering the first and second data sets, in this embodiment, can be thought of as registering two vector loops 210, one from the first data set and one from the second data set. The first and second heart vector data sets each comprise a matrix L. Matrix L is transferred to vector matrix F ($F_1$ and $F_2$ are used hereafter to denote the vector matrix corresponding to the first and second heart vector data sets, respectively) using equation (1):

$$F = A_T [L_1, L_2, \ldots L_M]^T \qquad (1)$$

In equation (1), F is a matrix with orthogonal lead vectors. $L_i$ are multiple lead vectors with length N that are in matrix L. N denotes the number of samples taken in each QRS portion. $A_T$ is the transfer matrix that is N-by-M in size. T is the matrix transpose operator.

In general, rotational changes of a first vector loop (the first vector loop generally corresponds to the first heart vector data set, e.g., matrix $F_1$) and a second vector loop (the second vector loop generally corresponds to the second heart vector data set, e.g., matrix $F_2$) are modeled by the orthonormal, 3-by-3 matrix R. In an alternative embodiment, matrix R can be represented by three different rotation angles. A scalar amplitude factor $\beta$ is included to account for expansion and contraction differences between the first and second loops. Although $F_1$ is initially assumed to be reasonably well synchronized in time to $F_2$, a desirable synchronization is introduced by the shift matrix $J_\tau$. Accordingly, matrix R can be used to account for rotational changes in the first and second vector loops, $\beta$ can be used to account for expansion and contraction of the loops, and $J_\tau$ can be used to synchronize the loops with respect to time. Assuming that additive Gaussian noise, W, is present, an equation used to register the first and second loops is:

$$F_2 = \beta R F_1 J_\tau + W \qquad (2)$$

The matrix $F_2$ and W are 3-by-N in size where N is the number of samples taken in the QRS portion of the cardiac cycle. Due to time synchronization, however, matrix $F_1$ may include additional samples ($(N+2\Delta)$ samples for each lead 82). Accordingly, the first vector loop (e.g., $F_2$) can be modeled from any of the $(2\Delta+1)$ synchronization positions in $F_1$.

In one embodiment, the first and second loops are aligned over the early part of the QRS portion of the cardiac cycle. Due to the time synchronization of the first and second vector loops by $J_\tau$, it is desirable to consider an error criterion for alignment which accounts for relatively large differences in amplitude.

In one embodiment, a criterion in which the Frobenius norm for the difference between $F_2$ and $\beta R F_1 J_\tau$ is normalized with the scaled and rotated reference loop $\beta R F_1 J_\tau$ as shown by equation (3):

$$\varepsilon_{min}^2 = \min_{\beta,R,\tau} \frac{\|F_2 - \beta R F_1 J_\tau\|_F^2}{\|\beta R F_1 J_\tau\|_F^2} \qquad (3)$$

Equation (3) may be minimized by first rewriting equation (3) as:

$$\varepsilon^2 = \frac{tr(F_2^T F_2) + \beta^2 tr(J_\tau^T F_1^T F_1 J_\tau) - 2\beta tr(F_2^T R F_1 J_\tau)}{\beta^2 tr(J_\tau^T F_1^T F_1 J_\tau)} \qquad (4)$$

Minimization with respect to R is equivalent to maximizing the rightmost term in the numerator. It should be noted that tr denotes the matrix trace. By introducing the matrix shown in equation (5)

$$B_\tau = F_2 J_\tau^T F_1^T \qquad (5)$$

it can be shown that the rotation matrix, for a fixed $\tau$, is estimated by equation (6)

$$\hat{R}_\tau^T = UV^T \qquad (6)$$

where the matrices U and V result from singular value decomposition of $R_\tau$, i.e., $R_\tau = U\Sigma V^T$.

The value of $\beta$ may be estimated by differentiating $\epsilon^2$ with respect to $\beta$ and setting the resulting expression equal to zero. The scale factor is estimated by $$\hat{\beta}_\tau = \frac{tr(F_2^T F_2)}{tr(F_2^T \hat{R}_\tau F_1 J_\tau)} \qquad (7)$$

The time synchronization parameter $\tau$ may be obtained by a grid search over all possible values of $\tau$, as represented by equation (8)

$$\hat{\tau} = \underset{\tau}{\operatorname{argmin}} \frac{\left\| F_2 - \hat{\beta}_\tau \hat{R}_\tau F_1 J_\tau \right\|_F^2}{\left\| \hat{\beta}_\tau \hat{R}_\tau F_1 J_\tau \right\|_F^2} \qquad (8)$$

Using equation 8, the optimal estimates of R and $\beta$ may be acquired.

In order to get an angular time series, the rotation matrix R is computed for each loop occurring at time $t_i$. The corresponding rotation angles can be estimated from $\hat{R}(t_i)$ as, $$\hat{\varphi}Y(t_i) = \arcsin(\hat{r}_{(1,3)}(t_i)) \qquad (9)$$

$$\hat{\varphi}X(t_i) = \arcsin\left(\frac{\hat{r}_{(1,2)}(t_i)}{\cos\hat{\varphi}Y(t_i)}\right) \qquad (10)$$

$$\hat{\varphi}Z(t_i) = \arcsin\left(\frac{\hat{r}_{(2,3)}(t_i)}{\cos\hat{\varphi}Y(t_i)}\right) \qquad (11)$$

where $\hat{r}_{(m,n)}(t_i)$ denotes the element in the $m^{th}$ row, $n^{th}$ column in matrix $\hat{R}(t_i)$. The estimated rotation angels along the X, Y, and Z axes can be used to register the representation of probe 56 with the image by, for example, rotating the image according to the estimated rotation angles.

In another embodiment, minimization of the error may be accomplished using a non-normalized least-squares method as shown by equation (12)

$$\varepsilon_{min}^2 = \min_{\beta,R,\tau} \| F_2 - \beta R F_1 J_\tau \|_F^2 \qquad (12)$$

In this embodiment, the estimate of $R_\tau$ is the same as that shown in equation (6), (of course, the optimum value may be conditioned on a different $\tau$), however, the amplitude factor is instead given by $$\hat{\beta}_\tau = \frac{tr(F_2^T \hat{R}_\tau F_1 J_\tau)}{tr(J_\tau^T F_1^T F_1 J_\tau)} \qquad (13)$$

The optimum $\tau$ is found as that value which minimizes the Frobenius norm in equation (12), $$\hat{\tau} = \underset{\tau}{\operatorname{argmin}} \left\| F_2 - \hat{\beta}_\tau \hat{R}_\tau F_1 J_\tau \right\|_F^2 \qquad (14)$$

In addition to registering the representation of probe 56 with an image of or pertaining to heart 72, first and second heart vector data sets may be used to adjust the properties of the image (e.g., size, position, etc.) once it has been acquired. For example, the image is acquired using a suitable imaging modality such as CT or MR. As the image is acquired it is correlated to the first heart vector data set. Once the image is acquired then the image may be used in a later procedure (e.g., during an EP study). However, due to factors such as the position of patient 74, changes to the size and shape of the image due to image processing, etc, the image may not be similar in size or position to heart 72. This may be compensated for, however, by acquiring a second heart vector data set at the time of the later procedure. The second heart vector data set is compared to the first heart vector data set as described previously. Based on this comparison, it may be determined that the image should be expanded or contracted to more accurately reflect the size of heart 72. It may also be determined that the image should be rotated along any of the X, Y, or Z axes to provide a more accurate reflection of the position of heart 72. In another embodiment, the representation of probe 56 may be registered with the image using the first and second heart vector data sets or using one or more features 116 or heart 72.

Figure 8:
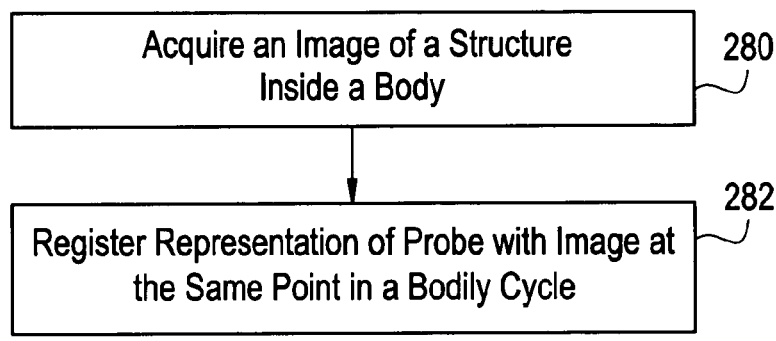
FIG. 8 shows a method for registering a representation of a probe with an image according to another embodiment.
Figure 9:
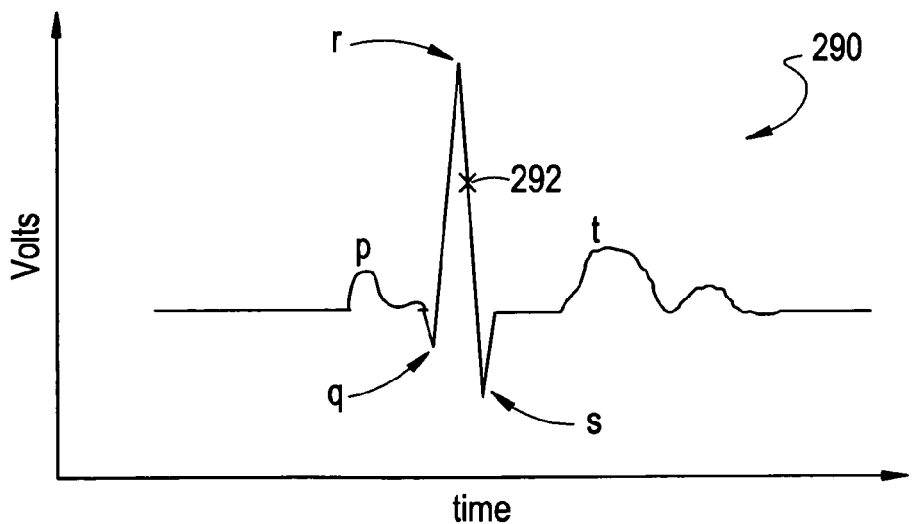
FIG. 9 shows a waveform of a bodily cycle according to one embodiment.

Referring to FIG. 8, a method is shown of registering a representation of probe 56 with an image according to another embodiment. In this embodiment, the representation of probe 56 is registered with an image of an organ or structure inside the body at substantially the same point in a bodily cycle. For example, in one embodiment, the organ or structure is heart 72 and the bodily cycle is a cardiac cycle shown in FIG. 9 by waveform 290 (e.g., ECG waveform).

At step 280, an image is acquired of the organ or structure. The image may be any of the various types and configurations of images described previously. In one embodiment, the acquisition of the image is correlated to a bodily cycle. For example, if the image is a CT image of heart 72, the CT equipment may be configured to acquire each slice of the image at a certain point in a cardiac cycle as shown by waveform 290. In one embodiment, a point 292 is chosen on the QRS portion of waveform 290 to correlate to the acquisition of the image. Of course, in other embodiments, the point may be located anywhere in the cardiac cycle. In additional embodiments, multiple images may be acquired that are correlated to multiple points in the bodily cycle.

In one embodiment, the image is acquired prior to probe 56 being inserted into the body of patient 74. In one typical example, an image of an organ or structure inside the body is taken in a radiology lab using a suitable imaging system (e.g., CT, MR, etc.). Patient 74 is then moved to the electrophysiology lab where the probe is inserted into the body of patient 74. The person 58 controlling the movement of probe 56 may then register the image and the representation of probe 56 on a display to substantially the same point in a bodily cycle as explained in connection with step 282. Of course, in other embodiments, the image may be acquired at any suitable time. For example, an ultrasound image may be acquired simultaneously with the insertion and/or manipulation of probe 56. In this instance, both the image and the location of probe 56 are being acquired and registered continually.

At step 282, the representation of probe 56 is registered with the image at point 292 in the cardiac cycle. In one embodiment, this is done by periodically acquiring the location of probe 56 at point 292 in the cardiac cycle and using these locations to display the representation of probe 56 on display 52. In this manner, the representation of probe 56 and the image are registered to substantially the same point in a bodily cycle.

In one embodiment, ECG leads are used to acquire information about the bodily cycle. Accordingly, when the image is being acquired, for example, ECG leads are used to simultaneously acquire information about the bodily cycle and time the acquisition of the image to the bodily cycle. The same or similar procedure may be used to time the acquisition of the location of probe 56 to the bodily cycle. In another embodiment, however, a blood pressure monitoring system may be used to acquire information about the bodily cycle. For example, a single pressure transducer patch may be located on a vein or artery that is adjacent to skin surface 78 of patient 74 (e.g., jugular vein, etc.). The readings obtained from the pressure transducer may be used to correlate the image and/or the location of probe 56 to a particular point in a cardiac cycle. In one embodiment, the device used (e.g., pressure transducer) to acquire information about the bodily cycle does not include any metallic portions or portions that may interfere with certain imaging systems (e.g., MR). Of course, multiple pressure transducers may also be used. A number of other suitable ways may also be used to acquire information about the bodily cycle.

In another embodiment, at least one image is acquired which is correlated to a point in a bodily cycle. The image may then be used to extrapolate the image to another point in the bodily cycle using information about how the image changes with respect to the bodily cycle. In another embodiment, at least two images may be acquired, each of which are correlated to different points in the bodily cycle. The images may then be used to interpolate and/or extrapolate to create an image at another point in the bodily cycle. The interpolated and/or extrapolated image which is correlated to the other point in the bodily cycle may then be registered to the representation of probe 56 at substantially the same point in the bodily cycle.

The construction and arrangement of the elements described herein are illustrative only. Although only a few embodiments have been described in detail in this disclosure, those of ordinary skill who review this disclosure will readily appreciate that many modifications are possible without materially departing from the novel teachings and advantages of the subject matter recited in the claims. Accordingly, all such modifications are intended to be included within the scope of the methods and systems described herein. The order or sequence of any process or method steps may be varied or re-sequenced according to alternative embodiments. Other substitutions, modifications, changes and omissions may be made in the design, operating conditions and arrangement of the embodiments without departing from the spirit and scope of the methods and systems described herein.

What is claimed is:

1. A method comprising:
    acquiring an image of or pertaining to a heart;
    acquiring a first data set pertaining to one or more locations of a heart vector of the heart, the first data set being spatially correlated with the image;
    acquiring a second data set pertaining to one or more locations of the heart vector of the heart;
    receiving first and second data sets at a processor; and
    registering, via the processor, a representation of a probe with the image by registering the location of the heart vector from the first data set with the location of the heart vector from the second data set, wherein the second data set is acquired using at least one lead positioned on a skin surface, wherein the location of the heart vector from the second data set can be determined relative to the lead, and wherein the location of the probe can also be determined relative to the lead.

2. The method of claim 1, wherein the image comprises one or more images obtained using computed tomography, magnetic resonance, or ultrasound.

3. The method of claim 1, wherein the acquiring the second data step and the registering step are performed on a repeating basis.

4. A method comprising:
    acquiring an image of or pertaining to a heart;
    acquiring a first and a second data set using a lead system;
    receiving the first and second data sets at a processor;
    registering, via the processor, a location of a first heart vector from the first data set relative the lead system at a skin surface of an imaged subject, wherein the first heart vector represents a summation of electrical currents at a particular time, the summation having a direction and an amplitude;
    registering, via the processor, a location of a second heart vector from the second data set relative to the lead system; and
    adjusting the size or position of the image dependent on a change in the location between the first and second heart vector generated from the first and second data sets, respectively.

5. The method of claim 4, further comprising registering a representation of a probe with an image, the probe being located in or adjacent to a heart.

6. The method of claim 4, wherein the image is correlated to a first heart vector data set and the image is adjusted by comparing the first heart vector data set to a second heart vector data set.

7. A system comprising:
    a lead system located at a skin surface of an imaged subject and operable to acquire a first data set and a second data set pertaining to one or more locations of a first and second heart vector, respectively, of the heart;
    a processor configured to be communicatively coupled to a probe and further configured to register the first heart vector from the first data set with the second heart vector from the second data set, the probe being configured to be located in or adjacent to a heart;
    memory configured to store:
    an image of at least a portion of the heart;
    the first data set pertaining to one or more locations of the first heart vector of the heart, the first data set being spatially correlated with the image;
    the second data set pertaining to one or more locations of the second heart vector of the heart; and
    a display configured to display the image and a representation of the probe, the image being registered with the representation of the probe by the registration of the first heart vector from the first data set with the second heart vector from the second data set, wherein the location of the heart vector from the second data set can be determined relative to the lead, and wherein the location of the probe can also be determined relative to the lead.

8. The system of claim 7, wherein the display is configured to display a map of electrical properties of the heart in conjunction with the image and representation of the probe.

9. The system of claim 7, wherein the first and second data sets are obtained using a plurality of electrocardiogram leads.

10. The system of claim 7, wherein the representation of the probe is registered with the image by registering the first heart vector from the first data set with the second heart vector from the second data set for at least a portion of the cardiac cycle.

11. The system of claim 10, wherein the portion of the cardiac cycle comprises at least a portion of the QRS segment.

12. The system of claim 7, wherein the system is an electrophysiology monitoring system.

13. The system of claim 7, wherein the second data set is spatially correlated with the probe.

* * * * *

UNITED STATES PATENT AND TRADEMARK OFFICE
CERTIFICATE OF CORRECTION

| | | |
|---|---|---|
| PATENT NO. | : 7,966,058 B2 | Page 1 of 1 |
| APPLICATION NO. | : 10/749540 | |
| DATED | : June 21, 2011 | |
| INVENTOR(S) | : Xue et al. | |

It is certified that error appears in the above-identified patent and that said Letters Patent is hereby corrected as shown below:

In Column 9, Line 56, delete "depolarization" and insert -- repolarization --, therefor.

In Column 13, Line 44, delete "angels" and insert -- angles --, therefor.

Signed and Sealed this
Twenty-seventh Day of March, 2012

David J. Kappos
*Director of the United States Patent and Trademark Office*